United States Patent

Feustel et al.

(10) Patent No.: US 9,452,981 B2
(45) Date of Patent: *Sep. 27, 2016

(54) PYROGLUTAMIC ACID ESTERS WITH IMPROVED BIODEGRADABILITY

(75) Inventors: Michael Feustel, Köngernheim (DE); Dirk Leinweber, Kelkheim (DE)

(73) Assignee: Clariant Produkte (Deutschland) GmbH, Frankfurt am Main (DE)

( * ) Notice: Subject to any disclaimer, the term of this patent is extended or adjusted under 35 U.S.C. 154(b) by 289 days.

This patent is subject to a terminal disclaimer.

(21) Appl. No.: 13/328,065

(22) Filed: Dec. 16, 2011

(65) Prior Publication Data

US 2012/0088942 A1    Apr. 12, 2012

Related U.S. Application Data

(62) Division of application No. 12/084,810, filed as application No. PCT/EP2006/010454 on Oct. 31, 2006, now abandoned.

(30) Foreign Application Priority Data

Nov. 12, 2005 (DE) .................. 10 2005 054 038

(51) Int. Cl.
*C09K 8/52* (2006.01)
*C07D 207/28* (2006.01)
*C08G 73/16* (2006.01)

(52) U.S. Cl.
CPC ......... *C07D 207/28* (2013.01); *C09K 2208/22* (2013.01)

(58) Field of Classification Search
CPC .... C09K 8/52; C09K 2008/22; C09K 8/528; C09K 3/00; C07D 207/28
USPC ............................................. 507/90; 528/289
See application file for complete search history.

(56) References Cited

U.S. PATENT DOCUMENTS

| | | | |
|---|---|---|---|
| 3,002,978 A | 10/1961 | Bocher | |
| 5,244,878 A | 9/1993 | Sugier et al. | |
| 6,093,862 A | 7/2000 | Sinquin et al. | |
| 6,566,309 B1 * | 5/2003 | Klug et al. | 507/90 |
| 2004/0106826 A1 * | 6/2004 | Kochat et al. | 562/571 |
| 2009/0124786 A1 | 5/2009 | Feustel et al. | |

FOREIGN PATENT DOCUMENTS

| | | |
|---|---|---|
| EP | 0 896 123 A1 | 2/1999 |
| WO | WO 93/25798 A1 | 12/1993 |
| WO | WO 94/12761 A1 | 6/1994 |
| WO | WO 94/24413 A1 | 10/1994 |
| WO | WO 2004/039314 A2 | 5/2004 |

OTHER PUBLICATIONS

International Search Report for PCT/EP2006/010455 mail dated Jan. 2, 2007.
International Preliminary Report on Patentability for PCT/EP2006/010455 issued Jun. 11, 2008.
CAS Registry No. 16891-48-8 Printout from ACS Copyright 2009.
Bullerwell, et al., "2-Mercaptoglyoxalines. Part VIII. The Preparation of 2-Mercaptoglyoxalines From Glutamic Acid", Journal of the Chemical Society, p. 3823ff, 1954.
Nájera, et al., Tetrahedron:Asymmetry, 10, (1999), pp. 2245-2303.
International Search Report for PCT/EP2006/010454 mail dated Apr. 17, 2007.
International Preliminary Report on Patentability for PCT/EP2006/010454 Apr. 17, 2007.
Fontan Yanes: Productos de Condensacion Del Acido Glutamico Con Glicoles: Revista de Plasticos Modernos, Madrid, ES, bd. 21,1970, Seiten 927-932, EP00908094 ISSN: 0034-8708 Seite 932.

* cited by examiner

*Primary Examiner* — Ling Choi
*Assistant Examiner* — Gennadiy Mesh
(74) *Attorney, Agent, or Firm* — Tod A. Waldrop

(57) ABSTRACT

A pyroglutamic acid ester of formula (1) in which A represents a $C_2$ to $C_4$ alkylene group; x represents a number from 1 to 100; R' represents an aliphatic, cycloaliphatic or aromatic radical that contains at least one structural unit of formula 2, and; y represents a number from 1 to 100. The use of these pyroglutamic acid esters in quantities of 0.01 to 2% by weight for preventing the formation of gas hydrates in aqueous phases that are connected to a gaseous, liquid or solid organic phase.

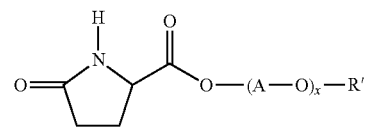

(1)

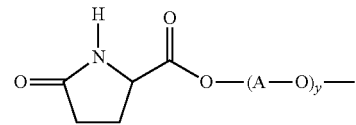

(2)

9 Claims, No Drawings

PYROGLUTAMIC ACID ESTERS WITH IMPROVED BIODEGRADABILITY

CROSS REFERENCE TO RELATED APPLICATION

This application is a divisional application of co-pending U.S. Ser. No. 12/084,810, filed May 29, 2008, entitled Pyroglutamic Acid Esters With Improved Biodegradability, the entire disclosure of which is hereby incorporated herein by reference.

The present invention relates to pyroglutamic esters and to their use as gas hydrate inhibitors.

Gas hydrates are crystalline inclusion compounds of gas molecules in water which form under certain temperature and pressure conditions (low temperature and high pressure). The water molecules form cage structures around the appropriate gas molecules. The lattice structure formed from the water molecules is thermodynamically unstable and is only stabilized by the incorporation of guest molecules. Depending on pressure and gas composition, these icelike compounds can exist even beyond the freezing point of water (up to above 25° C.).

In the mineral oil and natural gas industry, great significance attaches in particular to the gas hydrates which form from water and the natural gas constituents methane, ethane, propane, isobutane, n-butane, nitrogen, carbon dioxide and hydrogen sulfide. Especially in modern natural gas extraction, the existence of these gas hydrates constitutes a great problem, especially when wet gas or multiphasic mixtures of water, gas and alkane mixtures are subjected to low temperatures under high pressure. As a consequence of their insolubility and crystalline structure, the formation of gas hydrates leads here to the blockage of a wide variety of extraction equipment such as pipelines, valves or production equipment in which wet gas or multiphasic mixtures are transported over relatively long distances at relatively low temperatures, as occurs especially in colder regions of the earth or on the seabed.

Moreover, gas hydrate formation can also lead to problems in the course of the drilling operation to develop new gas or crude oil deposits at the appropriate pressure and temperature conditions by the formation of gas hydrates in the drilling fluids.

In order to prevent such problems, gas hydrate formation in gas pipelines, in the course of transport of multiphasic mixtures or in drilling fluids, can be suppressed by using relatively large amounts (more than 10% by weight, based on the weight of the aqueous phase) of lower alcohols such as methanol, glycol or diethylene glycol. The addition of these additives has the effect that the thermodynamic limit of gas hydrate formation is shifted to lower temperatures and higher pressures (thermodynamic inhibition). However, the addition of these thermodynamic inhibitors causes serious safety problems (flashpoint and toxicity of the alcohols), logistical problems (large storage tanks, recycling of these solvents) and accordingly high costs, especially in offshore extraction.

Attempts are therefore now being made to replace thermodynamic inhibitors by adding additives in amounts of <2% in temperature and pressure ranges in which gas hydrates can form. These additives either delay gas hydrate formation (kinetic inhibitors) or keep the gas hydrate agglomerates small and therefore pumpable, so that they can be transported through the pipeline (agglomerate inhibitors or antiagglomerants). The inhibitors used either prevent nucleation and/or the growth of the gas hydrate particles, or modify the hydrate growth in such a way that relatively small hydrate particles result.

The gas hydrate inhibitors which have been described in the patent literature, in addition to the known thermodynamic inhibitors, are a multitude of monomeric and also polymeric substance classes which are kinetic inhibitors or antiagglomerants. Of particular significance in this context are polymers having a carbon backbone which contain both cyclic (pyrrolidone or caprolactam radicals) and acyclic amide structures in the side groups.

For instance, WO-94/12761 discloses a process for kinetically inhibiting gas hydrate formation by the use of polyvinyllactams having a molecular weight of $M_w$>40 000 D, and WO-93/25798 discloses such a process using polymers and/or copolymers of vinylpyrrolidone having a molecular weight of $M_w$>5000 to 40 000 D.

EP-A-0 896 123 discloses gas hydrate inhibitors which may comprise copolymers of alkoxylated methacrylic acid without alkyl end capping and cyclic N-vinyl compounds.

U.S. Pat. No. 5,244,878 describes a process for retarding the formation or reducing the tendency to form gas hydrates. To this end, polyols which are esterified with fatty acids or alkenylsuccinic anhydrides are used. The compounds prepared do not have any amino acid functions which can interact with clathrates (cage molecules).

The additives described have only limited efficacy as kinetic gas hydrate inhibitors and/or antiagglomerants, have to be used with coadditives, or are unobtainable in a sufficient amount or obtainable only at high cost.

In order to be able to use gas hydrate inhibitors even in the case of greater cooling than currently possible, i.e. further within the hydrate region, a further enhancement of action is required in comparison to the prior art hydrate inhibitors. In addition, improved products are desired with regard to their biodegradability.

It was thus an object of the present invention to find improved additives which both slow the formation of gas hydrates (kinetic inhibitors) and keep gas hydrate agglomerates small and pumpable (antiagglomerants), in order thus to ensure a broad spectrum of application with high potential action. Furthermore, they should be capable of replacing the currently used thermodynamic inhibitors (methanol and glycols), which cause considerable safety problems and logistical problems.

Since currently used inhibitors such as polyvinylpyrrolidone and polyvinylcaprolactam have only a moderate biodegradability, the inventive compounds should additionally have an improved biodegradability.

The prior art discloses pyroglutamic esters which find use not as gas hydrate inhibitors but rather in other fields.

For instance, U.S. Pat. No. 3,565,794 discloses esters and amides of pyroglutamic acid which comprise amino, alkoxy, aryloxy, cycloalkoxy or heteroalkoxy groups and their use as a selective solvent for hydrocarbons in aromatics extraction.

U.S. Pat. No. 4,774,255 discloses pyroglutamic esters of α-hydroxycarboxylic acids which are in turn esterified with mono- or polyols. The resulting compounds always contain the same number of ester functions as they contain pyroglutamic acid structural units.

DE-A-25 58 909 discloses compounds which form through reaction of pyroglutamic acid with mono- or polyhydric alcohols, and subsequent alkoxylation of the resulting ester. These compounds are alkoxylated on the nitrogen atom of the pyroglutamic acid and do not contain any alkoxy groups that bind the pyroglutamic acid structural units to the alcohol structural units.

DE-A-21 02 171 discloses pyroglutamic esters with saturated $C_{19}$- to $C_{30}$-alcohols and their therapeutic and cosmetic use on the skin.

JP-A-48 082 046 discloses pyroglutamic esters of polyglycols with end-capping, and also polyols without alkoxy groups.

As has now been found, surprisingly, both water-soluble and oil-soluble pyroglutamic esters are suitable as gas hydrate inhibitors. According to the structure, these esters can delay both the nucleation and the growth of gas hydrates (kinetic gas hydrate inhibitors) and suppress the agglomeration of gas hydrates (antiagglomerants). In addition, the inventive compounds have a significantly improved biodegradability.

The present invention provides compounds of the formula 1

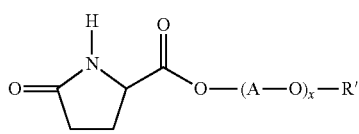
(1)

in which
A is a $C_2$- to $C_4$-alkylene group
x is from 1 to 100
R' is an aliphatic, cycloaliphatic or aromatic radical which contains at least one structural unit of the formula 2

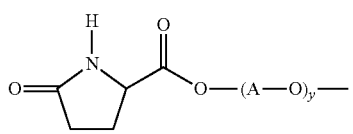
(2)

and
y is from 0 to 100.

The invention further provides for the use of compounds of the formula 1 in amounts of from 0.01 to 2% by weight (based on the weight of the aqueous phase) for preventing the formation of gas hydrates in aqueous phases which are in contact with a gaseous, liquid or solid organic phase.

The invention further provides a process for inhibiting the formation of gas hydrates by adding at least one compound of the formula 1 in amounts of from 0.01 to 2% by weight (based on the weight of the aqueous phase) to an aqueous phase which is in contact with a gaseous, liquid or solid organic phase and in which gas hydrate formation is to be prevented.

R' represents an organic radical which contains one or more structural units of the formula 2. It can generally by represented by the formula 3

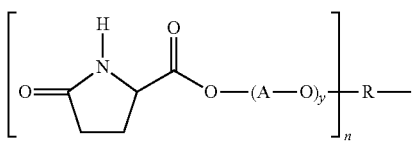
(3)

in which n is 1-100 and R is an aliphatic, cycloaliphatic or aromatic radical which may contain heteroatoms and bears at least (n+1) active hydrogen atoms which can be substituted by alkoxylation, and which bears n structural units of the formula 2. R is preferably an organic radical having from two to six active hydrogen atoms. The active hydrogen atoms may stem, for example, from hydroxyl groups, amino groups or carboxyl groups which are bonded to alkyl, alkenyl, cycloalkyl, aryl, alkylaryl or polyoxyalkylene radicals.

In a preferred embodiment, R is an organic radical having two active hydrogen atoms and up to 100 carbon atoms. Accordingly, n is then 1.

In a preferred embodiment of the invention, R is a radical which comprises at most one ester group or at most one carboxylic acid group. What is meant by this is that R comprises either one ester group or one carboxylic acid group or neither an ester group nor a carboxylic acid group. R may comprise any further substituents, for example amino or amido substituents. R is more preferably an alkylene or polyalkylene oxide radical having from 1 to 30 carbon atoms.

In a further preferred embodiment, R is a radical formed by formal abstraction of the hydrogen atoms of the OH groups of a polyol. Preferred polyols are ethylene glycol, propylene glycol, glycerol, diglycerol, triglycerol, tetraglycerol, polyglycerol, trimethylolpropane, pentaerythritol, dipentaerythritol, tripentaerythritol, sorbitol, sorbitan, diethylene glycol, triethylene glycol, propylene glycol, dipropylene glycol and tripropylene glycol. It is possible for all or only some of the hydrogen atoms of the polyols to be abstracted in the formation of R. It is preferred when 2, 3, 4, 5 or 6 hydrogen atoms of the OH groups of the polyols are abstracted, i.e. bear radicals of the formula 2.

R may also be a single bond. In this case, R' is reproduced by the formula 2.

A preferably represents ethylene radicals or mixtures of ethylene and propylene radicals.

In the alkoxy chain reproduced by $(A-O)_x$ or $(A-O)_y$, A is preferably an ethylene or propylene radical, especially an ethylene radical. x and y are preferably each independently from 1 to 80, in particular from 2 to 70, especially from 3 to 50. The alkoxy chain may be a block polymer chain which has alternating blocks of different alkoxy units, preferably ethoxy and propoxy units. It may also be a chain with a random sequence of the alkoxy units or a homopolymer.

In a preferred embodiment, $-(A-O)_x-$ or $-(A-O)_y-$ represents an alkoxy chain of the formula

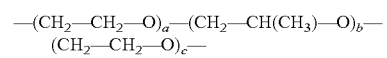

in which
a is from 1 to 100, preferably from 5 to 80,
b is from 0 to 100, preferably from 5 to 100,
c is from 1 to 100, preferably from 5 to 80.

In a further preferred embodiment, $-(A-O)_n-$ represents an ethoxy radical having from 1 to 100 ethoxy units.

It is common to all embodiments that preferably at least 50 mol % of the (A-O) radicals are ethoxy radicals; in particular, from 60 to 100 mol % are ethoxy radicals.

Examples of inventive compounds are specified in the formulae 4 and 5 which follow:

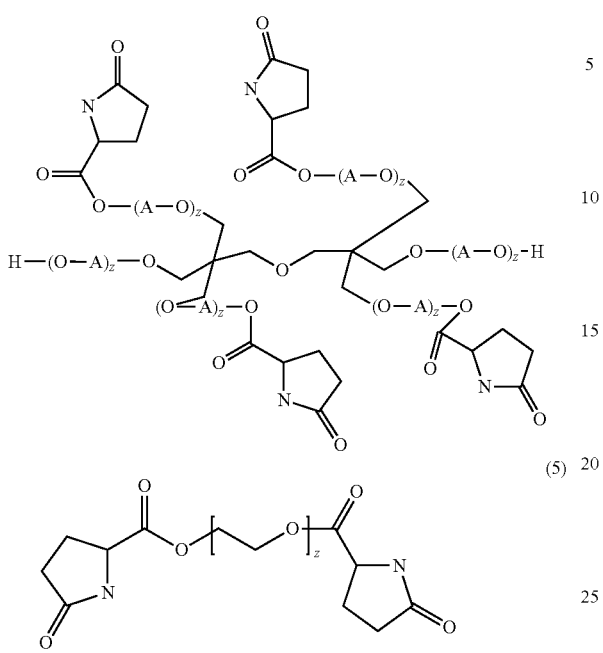

(4)

(5)

in which z may assume the values specified for x and y. Formula 5 corresponds to the case when R is a single bond.

The inventive pyroglutamic esters are preparable by esterifying pyroglutamic acid (enantiomerically pure or racemic) or glutamic acid (preferably L-glutamic acid) with at least one alcohol of the formula HO-(A-O)$_x$—R—(O-A)$_y$-OH. The preparation of the inventive esters is known in the prior art and is effected by uncatalyzed or acid-catalyzed condensation of the carboxylic acid with the appropriate alcohol. The reaction temperature is generally between 100 and 300° C., preferably from 170 to 250° C.

The molar ratio employed in the esterification of OH groups in the alcohol to the pyroglutamic acid or glutamic acid is preferably between 1:0.3 and 1:1, especially between 1:0.5 and 1:1.

The reaction can be carried out at atmospheric pressure or reduced pressure. The catalyzing acids include, for example, HCl, $H_2SO_4$, sulfonic acids, $H_3PO_4$ or acidic ion exchangers, which are used in amounts of from 0.1 to 5% by weight, based on the weight of the reaction mixture. The esterification takes generally from 3 to 30 hours.

To prepare the inventive pyroglutamic esters, as well as pyroglutamic acid, it is also possible to use glutamic acid which is converted directly to the pyroglutamic ester. Accordingly, 2 mol of water of reaction are then formed per esterified alcohol function. In this case, the by-products formed may also be glutamic esters which, however, do not disrupt the inventive use of the pyroglutamic esters as gas hydrate inhibitors.

The inventive pyroglutamic esters can be used alone or in combination with other known gas hydrate inhibitors. In general, a sufficient amount of the inventive pyroglutamic ester will be added to the system prone to form hydrates that sufficient inhibition is obtained under the given pressure and temperature conditions. The inventive pyroglutamic esters are used preferably in amounts between 0.02 and 1% by weight (based on the weight of the aqueous phase). When the inventive pyroglutamic esters are used in a mixture with other gas hydrate inhibitors, the concentration of the mixture is from 0.01 to 2% by weight or from 0.02 to 1% by weight in the aqueous phase.

For use as gas hydrate inhibitors, the pyroglutamic esters are preferably dissolved in water-miscible alcoholic solvents, for example methanol, ethanol, propanol, butanol, ethylene glycol, and oxyethylated monoalcohols such as butylglycol, isobutylglycol, butyldiglycol.

EXAMPLES

Preparation of the Pyroglutamic Esters

Example 1

Preparation of Triethylene Glycol Di(Pyroglutamate)

In a 250 ml four-neck flask with stirrer, thermometer, nitrogen purge and distillation system, 129 g of pyroglutamic acid, 75 g of triethylene glycol and 1.0 g of p-toluenesulfonic acid were mixed and heated to 200° C. Within 8 h at 200° C., approx. 18 ml of water were distilled off. This afforded approx. 187 g of triethylene glycol di(pyroglutamate) with a hydrolysis number of 303 mg KOH/g.

Example 2

Preparation of Triethylene Glycol Di(Pyroglutamate)—Variant with L-Glutamic Acid In a 250 ml four-neck flask with stirrer, thermometer, nitrogen purge and distillation system, 147 g of L-glutamic acid, 75 g of triethylene glycol and 1.0 g of p-toluenesulfonic acid were mixed and heated to 200° C. Within 12 h at 200° C., approx. 36 ml of water were distilled off. This afforded approx. 187 g of triethylene glycol di(pyroglutamate) with a hydrolysis number of 303 mg KOH/g.

Example 3

Preparation of (Trimethylolpropane+9 EO) Tri(Pyroglutamate)

In a 500 ml four-neck flask with stirrer, thermometer, nitrogen purge and distillation system, 129 g of pyroglutamic acid, 265 g of trimethylolpropane+9 EO and 1.5 g of p-toluenesulfonic acid were mixed and heated to 200° C. Within 15 h, approx. 18 ml of water were distilled off at 200° C. This afforded approx. 376 g of (trimethylolpropane+9 EO) tri(pyroglutamate) with a hydrolysis number of 148 mg KOH/g.

Example 4

Preparation of (Sorbitol+18 EO) Tri(Pyroglutamate)

In a 1000 ml four-neck flask with stirrer, thermometer, nitrogen purge and distillation system, 129 g of pyroglutamic acid, 325 g of sorbitol+18 EO and 1.5 g of p-toluenesulfonic acid were mixed and heated to 200° C. Within 20 h at 200° C., approx. 18 ml of water were distilled off. This afforded approx. 436 g of (sorbitol+18 EO) tri(pyroglutamate) with a hydrolysis number of 127 mg KOH/g.

Example 5

Preparation of (Sorbitol+30 EO) Hexa(Pyroglutamate)

In a 500 ml four-neck flask with stirrer, thermometer, nitrogen purge and distillation system, 129 g of pyroglutamic acid, 250 g of sorbitol+30 EO and 1.0 g of p-toluenesulfonic acid were mixed and heated to 200° C. Within 20 h at 200° C., approx. 18 ml of water were distilled off. This afforded approx. 361 g of (sorbitol+30 EO) hexa(pyroglutamate) with a hydrolysis number of 154 mg KOH/g.

Example 6

Preparation of (Decaglycerol+30 EO) Poly(Pyroglutamate)

In a 1000 ml four-neck flask with stirrer, thermometer, nitrogen purge and distillation system, 129 g of pyroglutamic acid, 390 g of decaglycerol+30 EO and 1.5 g of p-toluenesulfonic acid were mixed and heated to 200° C. Within 30 h at 200° C., approx. 18 ml of water were distilled off. This afforded approx. 501 g of (decaglycerol+30 EO) poly(pyroglutamate) with a hydrolysis number of 112 mg KOH/g.

Example 7

Preparation of (Polypropylene Glycol 400+10 EO) Di(Pyroglutamate)

In a 1000 ml four-neck flask with stirrer, thermometer, nitrogen purge and distillation system, 129 g of pyroglutamic acid, 420 g of polypropylene glycol 400+10 EO and 1.5 g of p-toluenesulfonic acid were mixed and heated to 200° C. Within 18 h at 200° C., approx. 18 ml of water were distilled off. This afforded approx. 531 g of (polypropylene glycol 400+10 EO) di(pyroglutamate) with a hydrolysis number of 105 mg KOH/g.

Example 8

Preparation of (Polypropylene Glycol 600) Di(Pyroglutamate)

In a 500 ml four-neck flask with stirrer, thermometer, nitrogen purge and distillation system, 129 g of pyroglutamic acid, 300 g of polypropylene glycol 600 and 1.0 g of p-toluenesulfonic acid were mixed and heated to 200° C. Within 20 h at 200° C., approx. 18 ml of water were distilled off. This afforded approx. 411 g of (polypropylene glycol 600) di(pyroglutamate) with a hydrolysis number of 136 mg KOH/g.

Efficacy of the Polymers as Gas Hydrate Inhibitors

To investigate the inhibiting action of the polyesters, a stirred steel autoclave with temperature control, pressure and torque sensor with capacity 450 ml was used. For investigations of kinetic inhibition, the autoclave was filled with distilled water and gas in a volume ratio of 20:80; for investigations of agglomerate inhibition, condensate was additionally added. Finally, 50 bar of natural gas were injected.

Proceeding from a starting temperature of 20° C., the autoclave was cooled to 4° C. within 3 h, then stirred at 4° C. for 18 h and heated back to 20° C. within 2 h. At first, a pressure decrease corresponding to the thermal compression of the gas is observed. When the formation of gas hydrate nuclei occurs during the cooling time, the pressure measured falls, and a rise in the torque measured and a slight increase, in the temperature are observed. Without inhibitors, further growth and increasing agglomeration of the hydrate nuclei lead rapidly to a further rise in the torque. When the mixture is heated, the gas hydrates decompose, so that the starting state of the experimental series is attained.

The measure used for the inhibiting action of the polymer is the time from the attainment of the minimum temperature of 4° C. until the first gas absorption ($T_{ind}$) or the time until the torque rises ($T_{agg}$). Long induction times or agglomeration times indicate an effect as a kinetic inhibitor. The torque measured in the autoclave serves, in contrast, as a parameter for the agglomeration of the hydrate crystals. In the case of a good antiagglomerant, the torque which builds up after gas hydrates have formed is significantly reduced compared to the blank value. In the ideal case, snowlike, fine hydrate crystals form in the condensate phase, do not agglomerate and thus do not lead to blockage of the installations serving for gas transport and for gas extraction.

Test Results

Composition of the natural gas used:
methane 84.8%, ethane 9.2%, propane 2.6%, butane 0.9%, carbon dioxide 1.6%, nitrogen 0.9%.

The comparative substance used was a commercially available gas hydrate inhibitor based on polyvinylpyrrolidone. The dosage in all tests was 5000 ppm based on the water phase.

| Pyroglutamic ester from example | $T_{ind}$ (h) | $T_{agg}$ (h) |
| --- | --- | --- |
| Blank value | 0 | 0 |
| 1 | 6.9 | 7.2 |
| 2 | 7.3 | 7.4 |
| 3 | 8.9 | 9.0 |
| 4 | 8.5 | 8.8 |
| 5 | 7.4 | 7.7 |
| 6 | 9.0 | 9.1 |
| 7 | 5.7 | 6.0 |
| Comparative | 3.5 | 3.6 |

As can be seen from the above test results, the inventive pyroglutamic esters are effective as kinetic gas hydrate inhibitors, and show a significant improvement over the prior art.

In order to test the action as agglomerate inhibitors, the test autoclave used above was initially charged with water and white spirit (20% of the volume in a ratio of 1:2) and, based on the water phase, 5000 ppm of the particular additive were added.

At an autoclave pressure of 50 bar and a stirrer speed of 500 rpm, the temperature was cooled from initially 20° C. to 4° C. within 3 hours, then the autoclave was stirred at 2° C. for 18 hours and warmed up again. The agglomeration time until the occurrence of gas hydrate agglomerates and the torque on the stirrer which occurred at the time, which is a measure of the agglomeration of the gas hydrates, were measured.

The comparative substance employed was a commercially available antiagglomerant (quaternary ammonium salt).

| Pyroglutamic ester from example | $T_{agg}$ (h) | $M_{max}$ (Ncm) |
|---|---|---|
| Blank value | 0.1 | 15.9 |
| 7 | 4.3 | 1.9 |
| 8 | 3.5 | 1.1 |
| Comparative | 2.6 | 4.1 |

As can be seen from these examples, the torques measured are greatly reduced in comparison to the blank value in spite of gas hydrate formation. This suggests significant agglomerate-inhibiting action of the inventive products. In addition, the products, under the test conditions, also have significant action as kinetic inhibitors. All examples show significantly better performance than the commercially available antiagglomerant (comparative=state of the art).

The significantly improved biodegradability (to OECD 306) of the inventive compounds compared to the prior art (commercially available polyvinylpyrrolidone) is shown hereinafter.

| Pyroglutamic ester from example | Biodegradability 28 days (OECD 306) |
|---|---|
| Polyvinylpyrrolidone | 5 |
| 1 | 72 |
| 2 | 70 |
| 3 | 65 |
| 4 | 78 |
| 5 | 58 |
| 6 | 42 |
| 7 | 47 |
| 8 | 25 |

The invention claimed is:

1. A method for inhibiting formation of a gas hydrate in an aqueous phase, the aqueous phase being in contact with a gaseous, liquid or solid organic phase comprising an alkane or a mixture of alkanes, the method comprising adding to the aqueous phase pyroglutamic acid ester compound of the formula

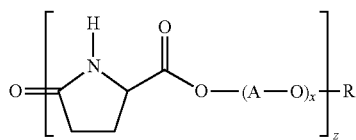

in which
A is a $C_2$- to $C_4$-alkylene group;
x is from 1 to 100;
R is a residue derived from an aliphatic, cycloaliphatic or aromatic compound, the aliphatic, cycloaliphatic or aromatic compound having at least z active hydrogen atoms which can be substituted by alkoxylation; and
z is from 2 to 101, wherein at least 50 mol-% of the A groups are ethylene radicals.

2. The method as claimed in claim 1, in which R is derived from a compound selected from the group consisting of ethylene glycol, propylene glycol, glycerol, digycerol, triglycerol, tetraglycerol, polyglycerol, tri methylolpropane, pentaerythritol, dipentraerythritol, tripentaerythritol, sorbitol, sorbitan, diethylene glycol, triethylene glycol, propylene glycol, dipropyleneglycol and tripropylene glycol.

3. The method as claimed in claim 1, wherein the pyroglutamic acid ester is prepared by using L-glutamic acid in enantiomerically pure form.

4. The method as claimed in claim 1, wherein the pyroglutamic acid ester comprises a glutamic ester.

5. The method as claimed in claim 1, wherein x is from 2 to 80.

6. The method as claimed in claim 1, wherein 60 to 100 mol-% of the A groups are ethylene radicals.

7. The method as claimed in claim 1, wherein R is derived from a compound selected from the group consisting of glycerol, digycerol, triglycerol, tetraglycerol, polyglycerol, trimethylolpropane, pentaerythritol, dipentraerythritol, tripentaerythritol, sorbitol and sorbitan.

8. The method as claimed in claim 1, wherein z is 3, 4, 5 or 6.

9. The method as claimed in claim 1, wherein the pyroglutamic acid ester compound is added to the aqueous phase in an amount in the range of 0.01 to 2 wt-%.

* * * * *